(12) United States Patent
Kleinschmidt et al.

(10) Patent No.: US 8,496,003 B2
(45) Date of Patent: Jul. 30, 2013

(54) WICK FOR AN ANESTHETIC EVAPORATOR

(75) Inventors: Lothar Kleinschmidt, Krummesse (DE); Karl-Ludwig Gippert, Herrnburg (DE); Thorsten Bruhn, Lübeck (DE); Dirk-Stefan Reichert, Lübeck (DE); Michael Riecke, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 632 days.

(21) Appl. No.: 12/503,497

(22) Filed: Jul. 15, 2009

(65) Prior Publication Data

US 2010/0051028 A1    Mar. 4, 2010

(30) Foreign Application Priority Data

Aug. 29, 2008 (DE) .......................... 10 2008 045 081

(51) Int. Cl.
*A61M 16/01* (2006.01)
(52) U.S. Cl.
USPC .................................................... 128/204.13
(58) Field of Classification Search
USPC ............. 128/200.11–200.14, 200.21, 202.21, 128/203.12, 203.16–203.17, 204.13–204.14; 131/209; 261/100–101, 104, DIG. 65; 55/520; 210/493.4, 497.1
See application file for complete search history.

(56) References Cited

U.S. PATENT DOCUMENTS

| | | | | |
|---|---|---|---|---|
| 2,674,999 A * | 4/1954 | Cox | .......................... | 128/203.25 |
| 3,215,140 A | 11/1965 | Frederick | | |
| 3,534,732 A * | 10/1970 | Bickford | .................. | 128/203.14 |
| 3,630,438 A * | 12/1971 | Bickford | .................. | 236/53 |
| 3,651,805 A * | 3/1972 | Breiling | .................... | 128/203.25 |
| 3,671,024 A * | 6/1972 | Breiling | ...................... | 261/39.1 |
| 4,067,935 A * | 1/1978 | Jones et al. | ............. | 128/203.14 |
| 4,075,297 A | 2/1978 | Seidel | | |
| 4,421,477 A * | 12/1983 | Adachi et al. | ................. | 431/325 |
| 4,693,853 A * | 9/1987 | Falb et al. | .................... | 261/39.1 |
| 4,774,032 A | 9/1988 | Coates et al. | | |
| 4,879,997 A * | 11/1989 | Bickford | .................. | 128/200.21 |
| 5,490,500 A * | 2/1996 | Reichert et al. | .......... | 128/204.13 |
| 7,275,539 B2 * | 10/2007 | Gippert | .................... | 128/204.12 |
| 2006/0225735 A1 | 10/2006 | Bottom et al. | | |

FOREIGN PATENT DOCUMENTS

| | | |
|---|---|---|
| DE | 25 07 262 | 9/1976 |
| EP | 1530980 A1 | 5/2005 |
| GB | 1307905 A | 2/1973 |
| GB | 1487042 A | 9/1977 |
| GB | 2177007 A | 1/1987 |
| GB | 24 21 691 A | 7/2006 |
| JP | 62502668 A | 10/1987 |

* cited by examiner

*Primary Examiner* — Jackie Ho
*Assistant Examiner* — Mark Wardas
(74) *Attorney, Agent, or Firm* — McGlew and Tuttle, P.C.

(57) ABSTRACT

A wick for an anesthetic evaporator is provided as a dimensionally stable wick body (14) transporting anesthetic by means of capillary force is provided. The wick body comprises a hollow cylinder as well as webs by which a gas-carrying cavity is formed.

13 Claims, 3 Drawing Sheets

WICK FOR AN ANESTHETIC EVAPORATOR

CROSS REFERENCE TO RELATED APPLICATIONS

This application claims the benefit of priority under 35 U.S.C. §119 of German Patent Application DE 10 2008 045 081.2 filed Aug. 29, 2008, the entire contents of which are incorporated herein by reference.

FIELD OF THE INVENTION

The present invention pertains to a wick for an anesthetic evaporator.

BACKGROUND OF THE INVENTION

Anesthetic evaporators for dispensing anesthetics frequently operate according to the "bypass principle," according to which a partial gas flow is branched off from a bypass line connecting the evaporator inlet and the evaporator outlet and is enriched with anesthetic vapor in an evaporator chamber. The partial gas flow enriched with anesthetic vapor is again mixed at the evaporator outlet with the gas flow flowing through the bypass line via a dispensing valve, which is connected to a setting wheel for setting the concentration of the anesthetic released. Helically arranged wick tubes, through which the partial gas flow is passed, are used to evaporate the anesthetic in the evaporator chamber. A tubular wick jacket, which presses the wick tube onto a wick holder, on the one hand, and dips with its free end into the liquid anesthetic, on the other hand, and transports anesthetic to the wick tubes by capillary action, is pulled over the wick tubes. On the way through the wick tube, the partial gas flow is enriched with anesthetic vapor up to the saturation limit. An anesthetic evaporator of this type is known from DE 25 07 262 B (corresponding to U.S. Pat. No. 4,075,297 which is incorporated by reference).

A wick tube as is used in the prior-art anesthetic evaporator can be manufactured at a high cost and requires a rather substantial manufacturing effort. Thus, wick material must at first be placed around a coil and fastened in the wick tube. The wick tube is then placed round the wick holder of the anesthetic evaporator such that the gas inlet for the partial gas flow into the evaporator chamber is located at the beginning of the wick tube and is not obstructed by wick material. When the wick jacket is subsequently pushed over the wick tube, the wick tube must not be displaced in relation to the wick holder.

SUMMARY OF THE INVENTION

The basic object of the present invention is to improve a wick of this type such that it can be manufactured at a low cost and can be mounted in a simple manner.

According to the invention, a wick is provided for an anesthetic evaporator. The wick comprises a dimensionally stable wick body transporting anesthetic by means of capillary force.

According to another aspect of the invention, a wick is provided for an anesthetic evaporator. The wick comprises a dimensionally stable wick body including porous means for transporting anesthetic by means of capillary force. The dimensionally stable wick body defines a gas cavity for passage of gas through the porous means for saturation of gas with transported anesthetic.

The wick body may advantageously comprise a hollow cylinder. The gas cavity may advantageously be defined by webs made in one piece with the wick body.

According to another further aspect of the invention, an anesthetic evaporator is provided comprising an evaporator pot defining an evaporator chamber and a compensator with an evaporator chamber gas inlet and a dispensing gas passage leading from the evaporator chamber. A wick is provided adjacent to the evaporator pot and the compensator, the wick comprising a dimensionally stable wick body including porous means for transporting anesthetic by means of capillary force and with the dimensionally stable wick body defining a gas cavity for passage of gas through the porous means for saturation of gas with transported anesthetic.

The advantage of the present invention is the design of the wick as a preferably one-piece, porous, dimensionally stable wick body, which can be directly connected to the corresponding connection component of the anesthetic evaporator. It is especially advantageous according to the invention to make gas ducts for passing through breathing gas in one piece with the wick body. The gas ducts are formed by webs, which are arranged either on the outside or on the inside of the wick body and are preferably manufactured as one assembly unit with the wick body. The gas ducts preferably extend helically at the wick body. However, routing the gas via a plurality of gas ducts, which are located one on top of another and are connected to each other, is possible as well. The wick body is preferably designed as a hollow cylinder or as a solid cylinder.

Other advantages of the wick according to the present invention are improved space utilization within the anesthetic evaporator, smoother surfaces to reduce flow resistances, simpler mounting and better thermal coupling of the wick body with the compensator of the anesthetic evaporator, with which the temperature effect is compensated.

It is especially advantageous that the wick body according to the present invention including the gas ducts can be manufactured from one piece. It may be an injection molding manufactured in a mold or a sintered shaped wick part. The gas-carrying area is formed here by a helical recess in the form of a groove in the shaped wick part. The liquid transport takes place by capillary action within the porous material. The capillary action can be varied by varying the density and the thickness of the wick body. As an alternative, the wick body may also be manufactured as a foam part or foamed part. Materials that are resistant to the anesthetics used are to be selected as the material for the wick body. Especially suitable are polyethylene, polypropylene, polytetrafluoroethylene, polyamide, special steel or even mixtures of these materials. Depending on the anesthetic used, bronze, copper, brass as well as sintered glass or sintered ceramic materials are suitable as well. The wick body is manufactured such that a sintered material is pressed from a preferably spherical granular product. The sintered compact is dimensioned such that its mean or typical pore size has a value of less than or equal to 30 μm. As an alternative to granular material, the wick body may also consist of an agglomeration of fine wires or fiber-like materials.

It is especially advantageous to arrange sealing lips, which come into contact either with the evaporator pot in the case of webs located on the outside or with the wick holder in case of webs located on the inside or with the compensator, at the webs pointing outwardly or inwardly, with which the gas ducts are formed. Gas tightness of the gas-carrying ducts against the evaporator pot or the wick holder or compensator is achieved in this manner so that the gas flows all the way through the gas ducts rather than flowing past the gas ducts at right angles to the longitudinal axis. Improvement of anesthetic uptake can be achieved by arranging obstacles within the gas ducts, because a turbulent flow develops as a result.

Gas-carrying ducts are provided within the wick body in another advantageous embodiment in order to enrich the gas flow with anesthetic vapor. Since the gas-carrying ducts are surrounded by the wick material on all sides in this embodiment, especially good saturation with anesthetic vapor is achieved.

One exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
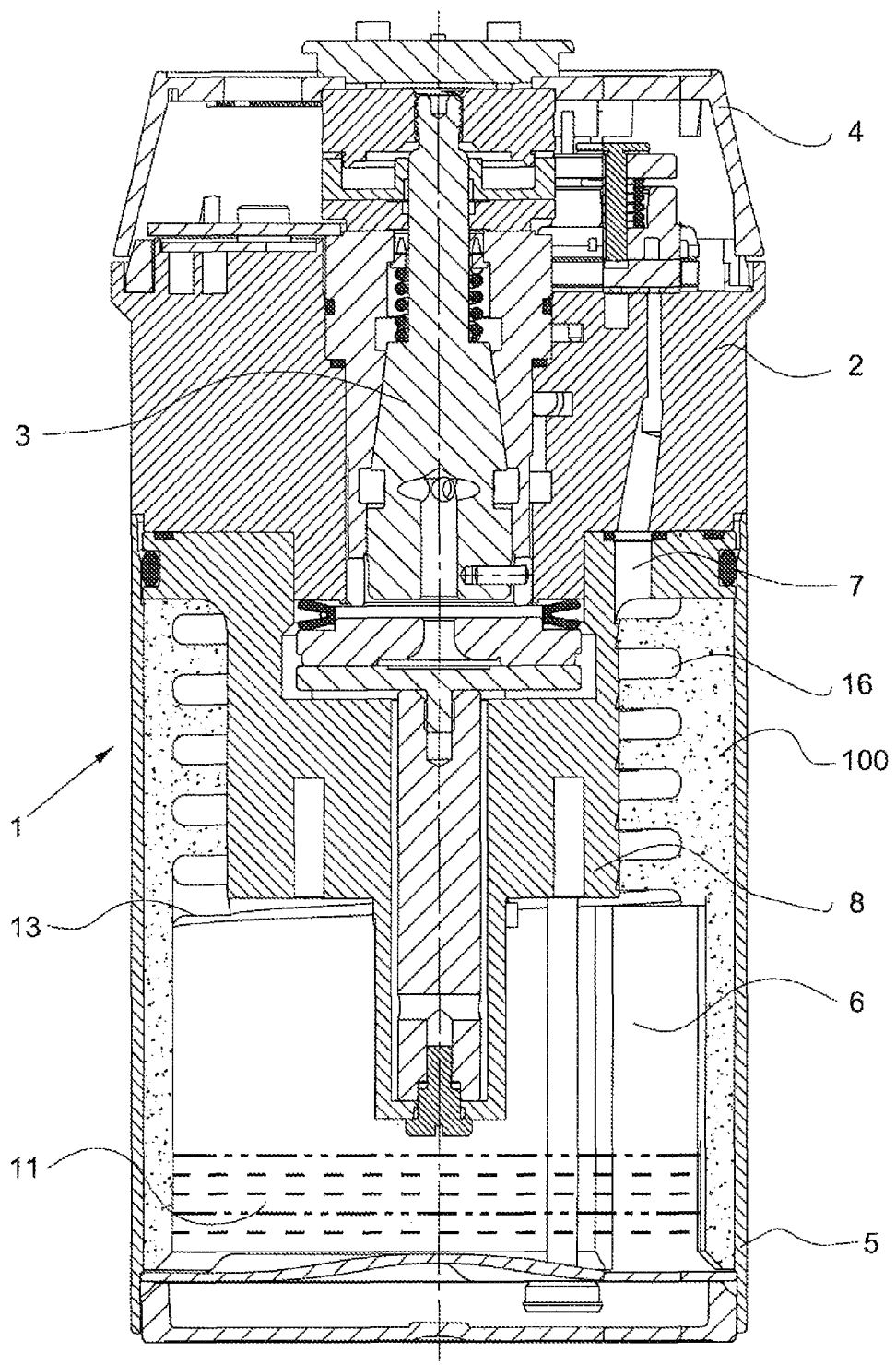
FIG. 1 is a schematic longitudinal sectional view of an anesthetic evaporator according to the invention.

Referring to the drawings in particular, FIG. 1 schematically shows an anesthetic evaporator according to the invention. An evaporator pot 5 defines an evaporator chamber 6. The evaporator pot 5 is located under an evaporator upper part 2 with a dispensing cone 3 for dispensing breathing gas saturated with anesthetic vapor and with a setting wheel 4 connected to the dispensing cone 3. The invention provides an anesthetic evaporator wick structure 100 comprised of a cylindrical wick body (14, 21) and helically extending cavity 16 (shown schematically as a vertically extending box in FIG. 1) described below. The dimensionally stable wick body 14, 21 is porous and transports anesthetic by means of capillary force. The evaporator wick structure 100, namely the cylindrical wick body 14, 21 is designed in terms of its principal geometry as a hollow cylinder.

The anesthetic evaporator wick structure 100 is provided radially outwardly of a compensator 8 and extends into the evaporator chamber 6. The anesthetic evaporator wick structure 100 dips into liquid anesthetic 11 in the chamber 6. The anesthetic 11 is transported by capillary transport to the helically extending cavity 16. The breathing gas to be enriched with anesthetic helically extending cavity 16 via the evaporator chamber inlet bore 7 and leaves same via an outlet opening 13.

Figure 2:
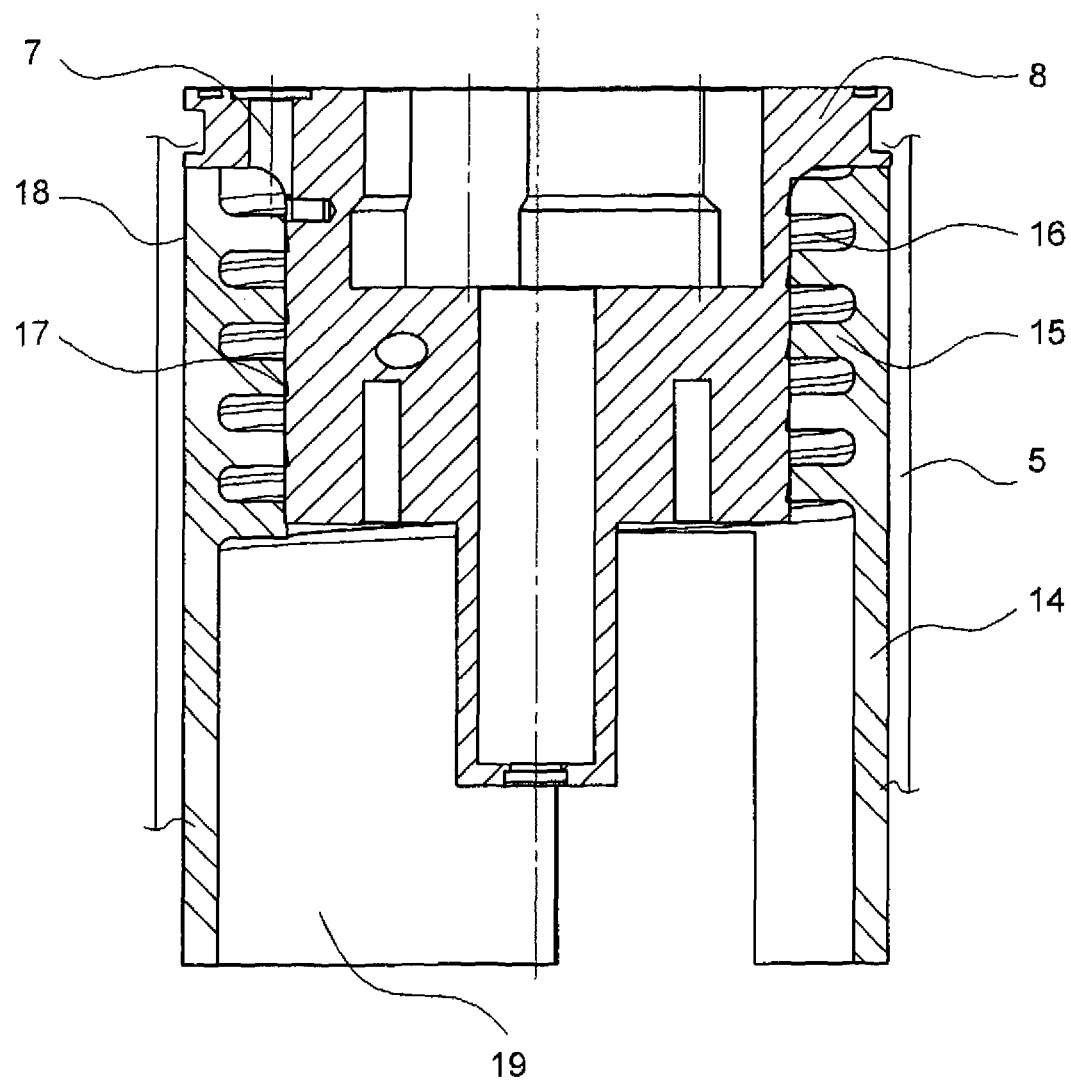
FIG. 2 is a view showing a wick body with gas-carrying ducts located on the inside as well as the evaporator pot and compensator of an anesthetic evaporator, according to an embodiment of the invention.

FIG. 2 shows a longitudinal section of a cylindrical wick body 14 according to the present invention, which is designed as a hollow cylinder. The wick body 14 has, on its inside, helically extending webs 15, by which the likewise helically extending cavity 16 is formed, which acts as a gas duct for the breathing gas to be enriched with anesthetic 11. Sealing lips 17, which are in contact with the compensator 8, are arranged at the free ends of the webs 15. The outer surface 18 of the wick body 14 is in contact with the evaporator pot 5. The underside 19 of the wick body 14 dips into the anesthetic 11, and is brought by capillary transport within the wick body 14 into the area of the webs 15. The breathing gas flows, beginning from the evaporator chamber inlet bore 7, through the cavity 16 and into the evaporator chamber 6, FIG. 1.

Figure 3:
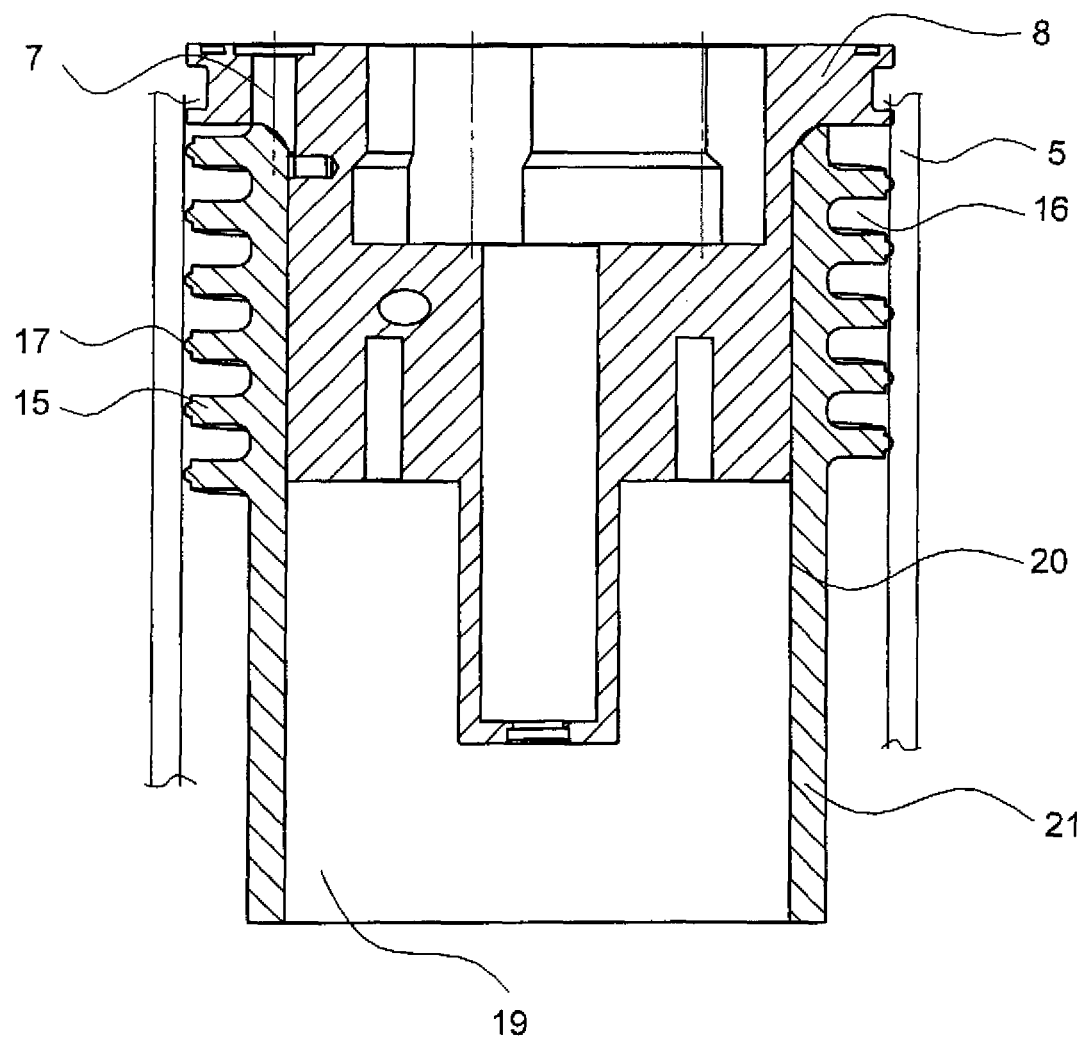
FIG. 3 is a view showing a wick body with gas-carrying ducts located on the outside as well as the evaporator pot and compensator of an anesthetic evaporator, according to another embodiment of the invention.

FIG. 3 shows an alternative embodiment of a wick body 21, in which the webs 15, which form the gas ducts, are arranged on the outside of the wick body 21. The inner surface 20 of the alternative wick body 21 is in contact with compensator 8, FIG. 1. The free ends of the webs 15 have sealing lips 17, which are in contact with the evaporator pot 5. Gas tightness of the cavity 16 against the evaporator chamber 6 is thus achieved.

While specific embodiments of the invention have been shown and described in detail to illustrate the application of the principles of the invention, it will be understood that the invention may be embodied otherwise without departing from such principles.

What is claimed is:

1. A wick for an anesthetic evaporator, the wick comprising:
   a dimensionally stable single piece integral wick body transporting anesthetic by means of capillary force, wherein:
   the wick body comprises a hollow tubular body with an outer surface and an inner surface surrounding a hollow interior;
   one of the outer surface and the inner surface comprises a cylindrical surface; and
   another of the outer surface and the inner surface defines webs by which a gas-carrying passage cavity is formed, each of the webs extending one of radially outwardly from a remaining portion of the outer surface of the wick body and radially inwardly from a remaining portion of the inner surface of the wick body.

2. A wick in accordance with claim 1, wherein the webs extend helically at the wick body as a continuous helical web.

3. A wick in accordance with claim 1, wherein a gas-carrying cavity extends within the wick body hollow interior.

4. A wick in accordance with claim 1, wherein the wick body consists of a porous material.

5. A wick in accordance with claim 4, wherein the wick body is made of sintered material.

6. A wick in accordance with claim 4, wherein the wick body comprises an agglomeration of fine wires or fiber-like materials.

7. A wick in accordance with claim 4, wherein the wick body comprises at least one of: polyethylene, polypropylene, polytetrafluoroethylene, polyamide, special steel, bronze, copper, and brass.

8. A wick in accordance with claim 4, wherein sintered glass or sintered ceramic materials are used as wick materials.

9. A wick in accordance with claim 1, wherein the wick body has a mean pore size of less than or equal to 30 μm.

10. A wick for an anesthetic evaporator, the wick comprising:
    a dimensionally stable wick body comprising a porous integral and dimensionally stable single structural piece that transports anesthetic by capillary force and with said dimensionally stable wick body defining a gas carrying cavity defining a passage of gas through said porous integral and dimensionally stable single structural piece for saturation of gas with transported anesthetic, wherein:

the wick body porous integral and dimensionally stable single structural piece comprises a hollow tubular body with an outer surface and an inner surface surrounding a hollow interior;

one of the outer surface and the inner surface comprises a cylindrical surface; and one of the outer surface and the inner surface defines webs by which a gas-carrying passage cavity is formed, each of the webs extending one of radially outwardly from a remaining portion of the outer surface of the wick body and radially inwardly from a remaining portion of the inner surface of the wick body.

11. An anesthetic evaporator comprising:

an evaporator pot defining an evaporator chamber;

a compensator with an evaporator chamber gas inlet and a dispensing gas passage leading from said evaporator chamber; and a wick adjacent to said evaporator pot and said compensator, said wick comprising an integral single piece dimensionally stable porous wick body transporting anesthetic by capillary force and with said dimensionally stable wick body defining a gas carrying cavity for passage of gas through said porous wick body for saturation of gas with transported anesthetic, wherein:

the integral single piece dimensionally stable porous wick body comprises a hollow tubular body with an outer surface and an inner surface surrounding a hollow interior;

one of the outer surface and the inner surface comprises a cylindrical surface;

one of the outer surface and the inner surface defines webs by which a gas-carrying passage cavity is formed, each of the webs extending one of radially outwardly from a remaining portion of the outer surface of the wick body and radially inwardly from a remaining portion of the inner surface of the wick body; and said gas carrying cavity defined by said webs cooperates with a surface of one of said evaporator pot and said compensator to form a gas carrying passage bordered by said integral single piece dimensionally stable porous wick body and said surface of one of said evaporator pot and said compensator.

12. A wick in accordance with claim 10, wherein the webs extend helically at the wick body as a continuous helical web.

13. An anesthetic evaporator in accordance with claim 11, wherein the webs extend helically at the wick body as a continuous helical web.

* * * * *